US008969032B2

(12) United States Patent
Grossmann

(10) Patent No.: US 8,969,032 B2
(45) Date of Patent: Mar. 3, 2015

(54) METHOD AND SYSTEM FOR THE GAS-TIGHT PROCESS CONTROL OF PERCOLATORS IN A BIOGAS METHOD HAVING TWO OR MORE STAGES

(75) Inventor: Jochen Grossmann, Dresden (DE)

(73) Assignee: GICON Grossman Ingenieur Consult GmbH, Dresden (DE)

( * ) Notice: Subject to any disclaimer, the term of this patent is extended or adjusted under 35 U.S.C. 154(b) by 161 days.

(21) Appl. No.: 13/696,169

(22) PCT Filed: May 6, 2011

(86) PCT No.: PCT/EP2011/057282
§ 371 (c)(1),
(2), (4) Date: Nov. 5, 2012

(87) PCT Pub. No.: WO2011/138426
PCT Pub. Date: Nov. 10, 2011

(65) Prior Publication Data
US 2013/0078700 A1    Mar. 28, 2013

(30) Foreign Application Priority Data

May 6, 2010    (DE) .......................... 10 2010 028 707

(51) Int. Cl.
*C12P 1/00*       (2006.01)
*C12P 39/00*      (2006.01)
(Continued)

(52) U.S. Cl.
CPC ............. *C12M 43/00* (2013.01); *C12M 21/04* (2013.01); *C12M 29/02* (2013.01); *C12M 45/06* (2013.01); *C12P 5/023* (2013.01); *C12M 23/58* (2013.01); *Y02E 50/343* (2013.01)
USPC ............................................. 435/41; 435/42

(58) Field of Classification Search
USPC .......................................................... 435/41
See application file for complete search history.

(56) References Cited

U.S. PATENT DOCUMENTS 4,652,374 A * 3/1987 Cohen ........................... 210/603
5,269,634 A    12/1993 Chynoweth et al.
(Continued)

FOREIGN PATENT DOCUMENTS

DE    10 2006 009 165 A1    1/2007
DE    10 2008 007 423 A1    8/2009
(Continued)

*Primary Examiner* — Sharmila G. Landau
*Assistant Examiner* — Sheridan Macauley
(74) *Attorney, Agent, or Firm* — Gudrun E. Huckett

(57) ABSTRACT

The invention relates to a method and a system for obtaining biogas in two or more stages in a hydrolysis and a methane stage, wherein the hydrolysis of solid biogenic materials is performed in at least two percolators operated at offset times. Liquid hydrolyzate and $CO_2$ rich hydrolysis gas, and then hydrolysis gas comprising methane thereby arises in the percolator. The liquid hydrolyzate is removed from the percolators, wherein part of the hydrolyzate is fed into the methane stage and the other part of the hydrolysis stage. In the methane stage, the hydrolyzate is converted to biogas and fermenting fluid. In the method according to the invention, the percolators are operated in a gas tight manner and hydrolysis gas is drawn off from the percolators, wherein the hydrolysis gas comprising methane is fed to an energy utilization and $CO_2$ rich hydrolysis gas is used for purging a further percolator operated at an offset time. The system according to the invention is suitable for performing said method and comprises at least two gas tight percolators that are interconnected by means of the gas supply lines thereof, and at least one methane reactor.

9 Claims, 5 Drawing Sheets

(51) Int. Cl.
*C12M 1/00* (2006.01)
*C12M 1/107* (2006.01)
*C12P 5/02* (2006.01)

(56) References Cited

U.S. PATENT DOCUMENTS

2005/0155928 A1* 7/2005 Jarventie .................. 210/603
2007/0158264 A1* 7/2007 Zhang ....................... 210/603
2009/0239209 A1* 9/2009 Lutz ............................. 435/3

FOREIGN PATENT DOCUMENTS

| | | |
|---|---|---|
| EP | 1 301 583 B1 | 4/2003 |
| EP | 2 103 681 A2 | 9/2009 |
| WO | 2006/048008 A2 | 5/2006 |
| WO | 2007/012328 A1 | 2/2007 |
| WO | 2010/028643 A2 | 3/2010 |

\* cited by examiner

METHOD AND SYSTEM FOR THE GAS-TIGHT PROCESS CONTROL OF PERCOLATORS IN A BIOGAS METHOD HAVING TWO OR MORE STAGES

BACKGROUND OF THE INVENTION

The invention relates to a method and a system for the percolation of solid biogenic material in a biogas method having two or more stages. The invention is applied in the area of renewable energy generation.

The production of biogas from renewable raw materials, from biologically available waste and other materials takes place using biogas plants, in which microorganisms transform said materials biochemically into biogas consisting of the main components methane and carbon dioxide.

The transformation. of biodegradable (henceforth "biogenic") material into biogas takes place in several biochemical steps, namely hydrolysis, acidogenesis, acetogenesis, and methanogenesis.

In hydrolysis, water-soluble components are dissolved from the biogenic material, and by a number of extracellular enzymes the non-water-soluble biogenic material is broken down into water-soluble, usually low-molecular, material. To speed up certain decomposition processes, so-called external enzymes may also be used. in the subsequent acidogenesis, the material dissolved during hydrolysis is converted into short-chain organic acids, such as short-chain fatty acids and amino acids. During acetogenesis the organic acids are converted into acetic acid, forming $CO_2$ in the process. The products of the acetogenesis are converted into methane during methanogenesis using methane bacteria.

In single-stage biogas plants, these processes take place in parallel as regards time and space. In two-stage biogas methods, the sub-steps of hydrolysis and acidogenesis (first stage) are separated from the sub-steps of acetogenesis and methanogenesis (second stage) as regards the technical apparatus and processes used. It is thereby possible to separately control the different environmental conditions for the conversion processes taking place respectively during hydrolysis and during methanogenesis This leads to an enhanced level of control and a higher stability of the method. Therefore biogas methods of two or more stages can yield higher methane concentrations in the biogas than single-stage biogas methods. As the hydrolysis process is separated technically, a variety of substrates may be transformed, so that a modular design of the biogas plant is possible.

In current language usage, the first stage of the two-stage biogas method is often simply referred to as the hydrolysis stage, and the second as the methane stage. The hydrolysis stage takes place in the so-called hydrolysis reactor. Methanation takes place in the so-called methane reactor. The aqueous solution leaving hydrolysis is commonly referred to as hydrolysate. In the following, this simplified language usage is adhered to.

In the hydrolysis reactor, the biogenic material is broken down into short-chain organic acids, while hydrolysis gas is formed. Usually, this hydrolysis gas is discharged from the process without being further utilized in the process.

For hydrolysis of solid biogenic material a variety of methods are suitable. Apart from hydrolysis in stirred tank reactors or plug-flow fermenters, methods using percolation are common. In percolation, the solid biogenic material is stacked in hydrolysis reactors, so-called percolators, and sprinkled with liquid (process water). The liquid formed during percolation, which is loaded with organic acids (hydrolysate, herein also referred to as percolate), is transported from the percolators into temporary storage tanks. The hydrolysate, which is stored in a corresponding hydrolysate tank, is fed into the methane reactor in a controlled manner. In this reactor, methane bacteria living under anaerobic conditions form the biogas containing methane. This feeding control makes the control of methane formation possible. According to the present state of knowledge, methane formation takes place in two ways, namely by acetotrophic and hydrogenotrophic transformation, which run in parallel in the methane reactor. The organic matter contained in the hydrolysate is thereby transformed into methane and into further by-products. The remaining liquid, largely freed from organic decomposition products of the biogenic material, is called fermentation liquid. The fermentation liquid is discharged from the methane reactor.

Hydrolysis of solid biogenic material is known from the state of the art and performed using the so-called aerobic percolation (herein also referred to as "open percolation" or "open hydrolysis"), In contrast to anaerobic methods, for which gas-tight percolators are essential, in aerobic percolation there is the possibility of air influx, and therefore the possibility of an aerobic transformation of organic components into carbon dioxide and water, and the possibility of a direct gas discharge into the atmosphere, resulting in losses of the potential biogas formation and in a continuous escape of formed hydrolysis gas. Hydrolysis gas present during aerobic operation contains mainly carbon dioxide and may also contain small amounts of hydrogen, methane, and traces of other gases, such as $H_2S$.

WO 2006/048008 and WO 2007/012328 A1 both describe two-stage biogas methods in which aerobic percolation is performed, so that the hydrolysis gas formed can escape into the atmosphere. The aerobic turnover of biogenic material results in the increased formation of carbon dioxide and water, and therefore the usable energy content of the substrate is disadvantageously reduced.

In addition to the biogas formed by methanation, the hydrolysis gas formed during percolation may partially also contain methane. This occurs especially when the supply of oxygen for percolation is restricted or prevented.

In an open percolation, any methane formed may escape into the atmosphere. This is a disadvantage for both the economic and ecological generation of biogas. It causes an additional pollution of the atmosphere with greenhouse gases and a reduced energy yield, since the corresponding amounts of methane are no longer available for energy recovery. Furthermore, the aerobic breakdown of biogenic material into carbon dioxide and water, which takes place with energy loss for the biogas process, is promoted by oxygen entry during aerobic percolation.

If the percolation is performed in a gas-tight manner and thus any oxygen entry into the percolators is restricted or completely prevented, the organic components are converted in an anaerobic manner. Two-stage biogas methods in which anaerobic percolation takes place are known, for instance, from DE 10 2006 009 165 A1. DE 10 2006 009 165 A1 discloses a method for the two-stage production of biogas from waste containing organic material and a reactor suitable for the operation of this method. The percolator is not ventilated, so that the hydrolysis process control takes place exclusively in an anaerobic manner. The hydrolysis gas formed thereby is discharged from the percolators and goes to waste.

By means of the anaerobic conversion of the organic materials used, the methane concentration in the hydrolysis gas can reach higher levels during anaerobic percolation than during aerobic percolation. There are methods known in which methane-forming microorganisms are added to the hydrolysis stage by inoculation, in order to allow production of energetically usable methane already during the hydrolysis stage of aerobic percolation methods.

Further, the conversion into methane can be achieved by means of increased residence time of the hydrolysate in the hydrolysis stage. To this end, DE 10 2008 007 423 A1 discloses a two-stage biogas method and a corresponding system, whereby at least part of the hydrolysis gas is transformed into thermal energy. The thermal energy produced from the hydrolysis gas is used to cover part of the energy requirements arising within the biogas plant. However, this thermal use of hydrolysis gas is disadvantageous if the methane content of the hydrolysis gas is low while at the same time its $CO_2$-content is high, since in this case an inert gas needs to be transported consuming energy.

The increased methane concentration inside the percolator may give rise to ignitable gaseous mixtures, once oxygen is introduced again. In the operation of percolators, the safety implications for this state need to be considered. If, in a gas-tight designed percolator, hydrolysis gas with safety-relevant methane concentrations is present, a safe discharge of the hydrolysis gas is necessary. Moreover, the methane concentration of the gas inside the percolator should be reduced sufficiently, especially prior to emptying the percolators, to be able to rule out an ignitable atmosphere on opening the tanks.

Therefore the gas contained in the percolator (herein also referred to as "gas atmosphere" of the percolator) is usually discharged before opening the percolator by burning it off using gas flares. To this end, in most cases the use of a further source of energy in the form of co-combustion is required, because the sole combustion of the gas is usually not possible.

To avoid the escape of safety-critical concentrations of methane from the gas-tight designed percolators, there are solutions known to reduce the methane concentration in the hydrolysis gas.

EP 1 301 583 B1 discloses a biogas plant designed for single-stage methanation by dry fermentation which distinguishes itself by its superior safety. To achieve this, the plant is equipped with a sensor that measures the partial pressure of oxygen in the fermenter. If the partial pressure of oxygen exceeds a certain limit value, this signals the entry of oxygen through a leak. The biogas pipe is automatically closed, and off-gas which mainly consists of carbon dioxide is fed in from a biogas-using facility. The gases present in the fermenter can escape through a purging valve, so that what remains in the tank in the end is almost exclusively carbon dioxide.

EP 2 103 681 A2 discloses a solution as a further development of the system of EP 1 301 583 B1, in which off-gas containing carbon dioxide from a combined heat-and-power plant (CHP) is used to expel biogas containing methane from a single-stage dry fermentation process. By doing so within a single biogas plant, both fermentation (anaerobic conversion of solid biogenic material into biogas from methane and carbon dioxide) and composting of the previously fermented substrate (aerobic process) can be performed without the necessity of turning the substrate for composting. This method is structured in such a way that in a process of single-stage biogas production, by the end of fermentation a purging of the has phase of the fermented takes place by feeding, in off-gas containing carbon dioxide from a CUP at the end of fermentation process. The methane concentration of the gas present in the fermenter is determined using a sensor. If the methane content of the gas exceeds a certain limit value (at which it makes sense to utilize the gas for energy recovery), the gas is fed into the CHP. If the value is below this limit, the gas is discharged and burned by a gas flare, which may involve feeding. in added fuel. If the methane content of the gas continues to fall below a second, lower, limit value (at which a safe gas discharge from the fermenter is possible), rather than off-gas containing carbon dioxide, fresh air is fed into the tormenter, and simultaneously the gaseous mixture is released into the environment through a biogas exhaust stack. By supplying fresh air it is also possible to run the composting process in the system.

The systems and methods disclosed in EP 1 301 583 B1 and EP 2 103 681 A2 represent single-stage biogas production processes which have the disadvantage that the methane concentration yielded in the biogas is limited. Furthermore, especially in the method of operation disclosed in EP 2 103 681 A2, energy needs to be expended to return $CO_2$-rich off-gas from the CHP to the reactors, thus reducing the overall efficiency of energy production in such a system.

The object of the invention is to make available a method and a system fix obtaining biogas in two stages, in which the gases formed during hydrolysis can be utilized better

SUMMARY OF THE INVENTION

This object is solved according to the invention by a method for obtaining biogas in two or more stages by hydrolysis of solid biogenic material in, at least two percolators operated at offset times, with the method comprising one hydrolysis stage and one methane stage. The biogenic material is thus hydrolyzed in the hydrolysis stage, whereby hydrolysate liquid and hydrolysis gas is formed in the percolator. in this process, first $CO_2$-rich hydrolysis gas is formed, and afterwards methane-containing hydrolysis gas is formed. The hydrolysate is removed from the percolators and collected, whereby one part of the hydrolysate is fed into the methane stage, and the other part of the hydrolysate is fed into the hydrolysis stage. In the methane stage, the hydrolysate is converted into biogas and fomentation liquid by means of methane-forming microorganisms. The fermentation liquid is removed from the methane reactor and collected, and is optionally fed into the hydrolysis stage. In the method according to the invention, the percolators are operated in a gas-tight manner, and hydrolysis gas is drawn off from the percolators By doing so, the methane-containing hydrolysis gas is used for energy recovery, and $CO_2$-rich hydrolysis gas from one percolator is used to purge another percolator, which is operated at offset times (as regards the percolator to he purged).

The invention is based on the observation that during the percolation of solid biogenic material increasing amounts of methane are formed especially towards the end of the percolation process, but at the start of the percolation process, hydrolysis gas with a high proportion of $CO_2$ is formed.

In the method according to the invention, this occurs due to the growth and the development of the microorganisms naturally occurring in the substrate and due to the hydrolysate and fermentation liquid being added during, the hydrolysis stage (this process control of the liquid is also referred to herein as "circular flow operation" of the respective liquid), The hydrolysate and fermentation liquid fed into the hydrolysis stage come from storage tanks which are arranged downstream of the hydrolysis stage (hydrolysate storage tanks) or of the methane stage (storage tanks for fermentation liquid).

This feeds methane-forming microorganisms from the methane stage into the hydrolysis stage, which convert, in the absence of oxygen within the gas-tight percolator of the hydrolysis stage, organic components of the hydrolysate into methane, In the method according to the invention, an additional inoculation with methane-forming microorganisms in the hydrolysis stage is not performed. The methane-forming microorganisms present in the percolator are present in the substrate or are fed into the percolator via the added fermentation liquid. In the method according to the invention, the hydrolysate is directly discharged from the hydrolysis stage. Preferably, no measures are taken to increase residence time of the hydrolysate in the hydrolysis stage, which would promote conversion of the hydrolysate components to methane in the hydrolysis stage. The methane formed in the hydrolysis stage in the method according to the invention is formed as a by-product of hydrolysis due to the process.

The process conditions of the method according to the invention are aimed at an intensive solute transport of water-soluble organic compounds from the solid biogenic materials used, into the hydrolysate liquid, which takes place by means of microbiological or enzymatic conversion processes. This is preferably realized by an acidic operation (pH value of the hydrolysate in the acidic range) Preferably, this operation takes place with a controlled slight oxygen supply (slightly aerobic).

The method according to the invention is a method of two or more stages to produce biogas, which comprises a hydrolysis stage and a methane stage, whereby only in the hydrolysis stage solid biogenic material is present. In the hydrolysis stage the biogenic material is decomposed by microbiological and enzymatic conversion processes, and water-soluble organic components are eluted from the biogenic material. These components, together with the watery liquid fed in for hydrolysis, form the hydrolysate. In the methane stage of the method according to the invention, organic components are fed in exclusively via the hydrolysate, i.e. via a watery liquid. In the method according to the invention, there are preferably no biogenic solids present in the methane stage.

When the method according to the invention is performed with more than one percolator, the percolators are either connected in parallel or serially with respect to hydrolysate control. By parallel connection of percolators in the sense of the invention is meant that the hydrolysate removed from the individual percolators is united before being, fed into the methane stage. By serial connection of percolators in the sense of the invention is meant that the hydrolysate removed from one percolator is fed into the liquids feed inlet of the percolator adjacent to it that has preferably been loaded with biogenic material at an earlier point in time.

The proportion of components (especially $CO_2$ and methane) in the hydrolysis gas is dependent on the solid biogenic materials (substrate) used.

The hydrolysis gas formed under anaerobic conditions at the start of the percolation process is $CO_2$-rich and is further characterized by its low methane content. This fraction of the hydrolysis gas is herein also referred to as $CO_2$-rich hydrolysis gas. $CO_2$-rich hydrolysis gas preferably has a $CO_2$-content of at least 50 vol.-%, preferably at least 70 vol.-%, and a methane content of less than 2 vol.-%, preferably less than 0.5 vol.-%. At the start of the percolation process, the pH value of the hydrolysate is in the slightly acidic range, preferably at pH 4 to pH 5 At this point in the process due to its low methane content it does not make sense to use the hydrolysis gas for energy recovery. Due to its high $CO_2$-content, this fraction of the hydrolysis gas is suitable for purging other percolators in this process.

As the conversion of biogenic material progresses during anaerobic percolation, the methane content of the hydrolysis gas increases, and its $CO_2$-content decreases. This fraction of the hydrolysis gas is herein also referred to as "methane-containing hydrolysis gas" Methane-containing hydrolysis gas preferably has a $CO_2$-content of less than 70 vol.-% and a methane content of at least 2 vol.-%, preferably of at least 8 vol.-%. Simultaneously with an increasing methane content of the hydrolysis gas, the pH value of the hydrolysate rises to the slightly acidic to neutral range; at this point in the percolation process, the pH value is preferably at pH>5. At this point in the process the methane-containing hydrolysis gas is drawn off by means of a method according to the invention, and used for energy recovery.

For energy recovery the methane-containing hydrolysis gas is optionally processed and purified, and utilized in a process common for energy recovery from biogas, for example as heating gas in CHPs, for feeding into the natural gas network, or for operating engines by combustion. Processing is performed preferably by using methods of gas scrubbing and/or pressure swing adsorption known from the state of the art. By doing so the content of associated gases in the methane-containing hydrolysis gas can be reduced, preferably its content of $CO_2$ and/or its content of $H_2S$.

As an alternative to being utilized directly for energy recovery, the hydrolysis gas containing methane is fed into the methane reactor prior to energy recovery, or it is united with the biogas formed in the methane reactor. Thereby strong fluctuations in the methane content of the biogas can be prevented.

In order to utilize the hydrolysis gas containing methane for energy recovery, in the method according to the invention the percolation is designed to be performed in a gas-tight manner, e the percolators are closed and equipped with gas pipes, which allow a controlled feed-in and draw-off of gas, for example via valves or gas flaps.

The percolation of the solid biogenic materials using a method according to the invention comprises within one percolator preferably the following steps of operation in chronological order:

a. Loading a percolator with the biogenic material (herein also referred to as feeding a percolator),
    Exhaust air mode,
    c. Gas utilising mode,
    d. Purging the percolator with exhaust air from another percolator that is operated at offset times,
    e. Purging the percolator with air,
    f. Opening the percolator, In exhaust air mode, $CO_2$-rich hydrolysis gas is drawn off from the percolator as exhaust air. The exhaust air mode is operated at the beginning of the percolation, as long as the hydrolysis gas formed contains a high $CO_2$-content. Therefore the exhaust air mode is preferably continued in operation until the methane concentration of the gas present within the percolator reaches a previously defined limit value and/or until the pH value of the hydrolysate reaches a previously defined limit value. The limit value for the methane concentration is substrate dependent and is preferably at least 1 vol.-% of methane, more preferably at least 2 vol.-% of methane. Utilisation of the hydrolysis gas for energy recovery makes sense preferably if the methane content of the hydrolysis gas is at least 8 vol.-%, The limit value for the pH value of the hydrolysate is also substrate-dependent and is preferably at most pH 5.

The $CO_2$-rich hydrolysis gas, which is drawn off from the percolator in exhaust air mode, is fed into another percolator (which is operated at offset times and about to be purged) as purging gas. In the method according to the invention, utilisation of the $CO_2$-rich hydrolysis gas for energy recovery is not intended.

The exhaust air mode is followed by the gas utilising mode, in gas utilising mode the hydrolysis gas is drawn off from the percolator and used for energy recovery. The gas utilising mode is in operation at that point in time during the percolation process when methane-containing hydrolysis gas is present within the percolator. Preferably, the gas utilising mode is continued in operation until the total amount of the hydrolysis gas formed, or the methane concentration of the gas present within the percolator, fall below their previously defined limit values, respectively. The methane-containing hydrolysis gas is drawn off from the percolator and subsequently used for as energy recovery. To this purpose, it is optionally united with the biogas that is formed in the methane stage of the biogas method according to the invention.

During purging in step d. of operation, the hydrolysis gas present in the percolator is first removed by expelling it by means of the fed-in purging gas. As purging gas, exhaust air from another percolator operated at offset times is used, which is running in exhaust air mode at this point in time. It is therefore required that there are at least two percolators in operation at offset times, with at least one percolator being in exhaust air mode. By in operation at offset times in the sense of the invention it is therefore understood that at least two percolators are loaded with solid biogenic materials at differing starting times and undergoing hydrolysis of their substrates, so that at least one percolator is in exhaust air mode.

As long as the gas atmosphere of the percolator contains a methane concentration sufficient to be energetically used and the methane concentration in the percolator indicates at least a safety-critical limit value, the gas atmosphere is used for gas utilisation (energy recovery). During purging in step d. the methane concentration in the gas atmosphere of the percolator decreases. Preferably, purging is continued until a complete exchange of the amount of gas present in the percolator has taken place, and the methane concentration of the gas atmosphere of the percolator has decreased sufficiently to be below a safety-critical limit value. The safety-critical limit value of the methane concentration is preferably below 1 vol.-%, more preferably at 20% of the lower explosion limit (LEL) for methane (corresponding to approximately 0.88 vol.-%).

During purging therefore the methane content of the gas atmosphere of the percolator decreases, and the $CO_2$-content of the gas atmosphere increases As long as the methane content of the gas exceeds a previously defined limit value, the expelled methane-containing hydrolysis gas is used fix energy recovery. Since over the course of purging the methane content of the gas continuously decreases, it does not make sense to utilize the gas for energy recovery when the methane content is too low. Therefore, the gas is drawn off from the percolator, preferably when it falls below a previously defined limit value of its methane concentration, without being used for as energy recovery. To identify this point of time in the process, the methane content of the gas present within the percolator is monitored, preferably continuously.

To reduce the content of the purging gas in the percolator, the percolator is purged with air before it is opened. To this end, ambient air is fed into the percolator, which expels the gaseous mixture of purging gas and hydrolysis gas from the percolator.

After purging the percolator is optionally opened and can be emptied subsequently and loaded again with fresh biogenic material. Opening takes place preferably when both the methane concentration and the $CO_2$-concentration in the percolator drop below a previously defined threshold value. The methane concentration is preferably less than 50% of the Occupational Exposure Limit (OEL), that is, preferably approximately 0.5 vol.-%.

The duration of percolation is dependent on the biogenic materials used. Preferably, the duration of one percolation (completion of the above-mentioned process steps a. to f.) is less than 30 days, preferably 14 to 25 days. Of these, the exhaust air mode comprises preferably the first five to nine days. When purging a percolator, the methane-containing hydrolysis gas present in the percolator to be purged is then removed by expelling it by means of exhaust air from a percolator operated at offset times and running in exhaust air mode.

To ensure that the exchange of gases between the then-connected percolators is directed one-way only, i.e. towards the percolator to be purged, the percolator operated at offset times, which is running in exhaust air mode, is preferably closed on the gas side before purging the percolator to be purged, so that overpressure arises in this percolator (which is in exhaust air mode). Subsequently, the exhaust air from the percolator operated at offset times is fed into the percolator to be purged, preferably after reaching, a threshold value of the pressure. This threshold value of the pressure is higher than the existing internal pressure in the percolator to be purged. Preferably, the threshold value of the pressure is at least 5 mbar overpressure, in comparison with the pressure inside the percolator to be purged; thus avoiding hydrolysis gas containing methane (from the percolator to be purged) from entering the percolator operated at offset times, which is running in exhaust air mode, and from possibly entering the atmosphere when drawn off as exhaust air.

The invention also includes a system for obtaining biogas in two or more stages, which is suitable for performing a method according to the invention.

The system according to the invention for obtaining, biogas in two or more stages comprises at least two percolators, especially solids percolators, each of which has one hydrolysate discharge pipe and one liquids feed inlet. The hydrolysate discharge pipe of a percolator is connected, via at least one hydrolysate storage tank, to at least one methane reactor.

The percolators in the system according to the invention are connected either in parallel or serially as regards hydrolysate control. In case of a parallel connection of the percolators, the hydrolysate discharge pipes of the percolators are preferably connected to at least one hydrolysate storage tank, in which the percolate from the different percolators is united. Percolators connected in parallel are characterized by a shared liquids feed inlet. Alternatively, or in addition to this, downstream to every percolator preferably a separate hydrolysate storage tank (herein "hydrolysate pre-storage tank") is arranged, whereby the hydrolysate pre-storage tanks are connected to the hydrolysate storage tank of the system via one liquids pipe, respectively.

In case of a parallel connection of the percolators, the hydrolysate discharge pipes of the percolators are connected, preferably via, a hydrolysate pre-storage tank, with the liquids feed inlet of the adjacent percolator, which has been loaded with biogenic material at an earlier point in time.

Downstream to the at least one methane reactor at least one storage tank for fermentation liquid is arranged. connected via a discharge pipe for fermentation liquid. In the system according, to the invention the hydrolysate storage tank and the storage tank for fermentation liquid are connected to the respective liquid feed inlets of the percolators. This allows a part of the hydrolysate and/or fermentation liquid to be fed into the percolators as process water for hydrolysis. If there are several methane reactors contained in the system according to the invention, then these are preferably connected liquid-side to the same hydrolysate storage tank and/or storage tank for fermentation liquid In the system according to the invention, the percolators are designed to be gas-tight and include each at least one closable gas supply pipe and at least one closable gas discharge pipe Each percolator is connected to a methane sensor which serves to measure the methane content of the gas present in the percolator. This sensor is preferably contained in a measuring device for determining the quality and quantity of the gas, with the device being connected to the respective percolator. Further, each percolator is connected to a pH sensor, which serves to measure the pH value of the liquid present in the respective percolator.

The closable as supply pipe of a percolator in the system according, to the invention is designed to allow switching to air supply or to purging gas supply. The at least two percolators are connected to each other via their gas supply pipes, so that during operation at offset times the feed-in of $CO_2$-rich hydrolysis gas from one percolator in exhaust air mode into a percolator to be purged can take place To this end, both gas supply pipes are switched to purging gas supply, so that an exchange of the gas atmospheres of both percolators is possible.

Every percolator in the system according to the invention is equipped with said features (gas-tight design with closable gas supply pipe and gas discharge pipe, methane sensor). The system according to the invention contains at least two, more preferably at least three percolators.

Percolators are known from prior art. They contain a grid, or a strainer bottom, on which the biogenic material is deposited. Further, they contain a feed inlet for process water, or percolate, and a percolate outlet. The percolators which are used in a system according to the invention are sealed in a gas-tight manner and contain a closable gas supply pipe and a closable gas discharge pipe, which allows an exchange of gases with the environment only after deliberate opening. Thus it is avoided that the biogenic materials to be percolated are continuously exposed to an aerobic atmosphere, which would promote their breakdown into carbon dioxide and water. The anaerobic atmosphere promotes increased formation of the low-molecular organic products required for methanation.

Closure of the gas pipes (gas supply pipes and gas discharge pipes), which are preferably designed in tubular form, is preferably effected by valves or gas flaps arranged on the supply and discharge pipes.

A percolator in a system according to the invention preferably contains a closable gas discharge pipe, which is designed to allow either switching to gas discharge into a system for energy recovery from the methane-containing hydrolysis gas (gas utilising system), or gas discharge into the atmosphere, or closure of the gas discharge pipe. Corresponding solutions for gas discharge to different means for utilisation are known from prior art. To this end, the gas discharge pipe preferably contains specially designed valves or gas flaps that allow switching. More preferably, a closable two-way valve is arranged on the gas discharge pipe for this purpose.

Preferably, the gas utilising system is a combined heat-and-power plant, a plant for producing biomethane ($CO_2$ scrubbing), or the methane reactor of the system according to the invention. Preferably, a gas storage tank is placed previous to the gas utilising system.

The system according to the invention is designed in such a manner that the liquids feed inlet of a percolator is suitable for feeding in hydrolysate and fermentation liquid into the percolator. For this purpose, the liquids feed inlet is connected to a hydrolysate storage tank and to a storage tank for fermentation liquid. This feature of the system according to the invention allows the circular flow operation of the liquids i.e. hydrolysate, fermentation liquid) in the method according to the invention.

Systems according to the invention contain at least two, preferably at least three, gas-tight designed percolators that are connected either in parallel or serially and that are connected to each other via their gas supply pipes, so that during operation at offset times the feed-in of $CO_2$-rich hydrolysis gas from one percolator in exhaust air mode into a percolator to be purged can take place. In percolators connected in parallel, via the hydrolysate discharge pipe the hydrolysate liquid is collected and united in a hydrolysate storage tank (liquid-side parallel connection) in contrast to serially connected percolators, in which the hydrolysate is discharged from one percolator and fed into another percolator operated at offset times, which latter has been loaded with biogenic materials at an earlier time point, in the case of a parallel connection the hydrolysate liquids from the individual percolators are united.

The percolators are connected to each other via a closable gas pipe which represents the respective as supply pipe of the percolator. The gas supply pipes are closable and designed to allow either switching to air supply, or to gas supply from another percolator, or closure of the gas supply pipe. Due to this design a controlled exchange of gases between the percolators is possible Preferably, valves or gas flaps serve as closures.

The percolators are operated at offset times. i.e. the loading with fresh biogenic material takes place in a staggered manner preferably at equal intervals. The hydrolysate liquid formed within the percolators is removed from the respective percolator via a hydrolysate discharge pipe, disposed into a hydrolysate storage tank. From there, a part of the liquid is fed into the methane reactor of the system according to the invention.

In further preferred systems according to the invention, a pressure sensor is arranged at each of the percolators which serves to measure the pressure inside the percolator.

The system according to the invention is operated as follows:

At least two percolators are loaded with solid biogenic material at offset times and then closed. Via the liquids feed inlet, the solid biogenic material (i.e. the substrate) is sprinkled with and passed by the process water (i.e. hydrolysate and fermentation liquid) which is operated in circular flow operation. By feeding in the liquid, the degradable components of the substrate are being converted to alcohols, sugars and short-chain fatty acids, thereby being transformed into a water-soluble form. The degradable components of the substrate that are dissolved in the liquid hydrolysate are removed from the percolator via the hydrolysate discharge pipe. The solid substrate is retained by means of the grid or strainer bottom.

The circular flow operation is realized by feeding liquid from the hydrolysate storage tank and/or the storage tank for fermentation liquid via the liquids feed inlet into the percolator. Afterwards the hydrolysate is fed into a hydrolysate storage tank, and then fed continuously into the methane reactor, where fermentation to &togas containing methane and carbon dioxide takes place.

The gas-tight closure of the percolators prevents any atmospheric oxygen from entering the percolators, and prevents any hydrolysis gas from escaping in an uncontrolled manner from the percolators.

During percolation, hydrolysis gas is formed, the chemical composition of which varies over the percolation period, After loading the percolator with biogenic material, at the start of percolation a $CO_2$-rich hydrolysis gas is formed. As the percolation continues, the $CO_2$ content of the hydrolysis gas decreases Simultaneously, the methane content of the hydrolysis gas increases. During this process, at first, among other substances, organic acids are formed as conversion products of the biogenic material, so that the pH value of the percolate is acidic As the percolation progresses, the pH value rises to a slightly acidic to neutral range.

In a percolator, preferably the following steps of operation are performed:

Exhaust air mode: The $CO_2$-rich hydrolysis gas formed at the start of percolation inside a percolator cannot be used for energy recovery and is disposed from the percolator via the gas discharge pipe. At this point in time the pH value of the hydrolysate is strongly acidic. A valve is opened in the gas discharge pipe so that the hydrolysis gas is disposed from the percolator as exhaust air.

Gas utilising mode: Over the further course of percolation, increasing amounts of methane are formed so that the methane content of the hydrolysis gas increases, while its $CO_2$ content decreases. if the methane content of the hydrolysis gas, which is being determined by the methane sensor in the measuring device, exceeds a defined limit, value, the gas discharge pipe is switched in such a manner as to connect the gas discharge pipe to a gas utilising system. Preferably, before this the hydrolysis gas is collected in a storage tank and processed in a gas treatment installation. At this point in time the pH value of the hydrolysate is in the neutral to slightly acidic range.

Purging with purging gas: Towards the end of percolation, only small amounts of organic degradation products of the biogenic material present in the hydrolysate are removed via the hydrolysate outlet. The pH value at the hydrolysate outlet is approaching the pH value present at the liquids feed inlet. The pH value of the liquid is measured using pH sensors in the liquids feed inlet and in the hydrolysate discharge pipe: However, the methane content of the hydrolysis gas continues to be very high. For expelling the remaining methane-containing hydrolysis gas from a percolator, exhaust air from another percolator (operated at offset times in relation to the percolator to be purged) is fed in as purging gas via the gas supply pipe, with the valve in opened position. Via an open valve in the gas discharge pipe, the gaseous mixture formed by hydrolysis gas and purging gas is fed from the percolator into the gas utilising system.

As soon as the methane concentration of the gaseous mixture formed by hydrolysis gas and fed-in purging gas inside the percolator reaches a previously defined lower limit value, the purging process with air is started. The methane concentration of the gaseous mixture in the percolator is thereby determined by means of the measuring device.

Purging with air: Ambient air is fed in via the gas supply pipe. The composition of gases present in the percolator is determined by means of the measuring, device. As soon as the concentration of methane and of $CO_2$ determined by the measuring device have each reached a previously defined minimal value, this signals that the percolator can be opened, emptied, and loaded again. This fresh loading marks the start of a new cycle consisting of Exhaust air mode, Gas utilising mode, Purging with purging gas, Purging with air, and Opening.

The method according to the invention allows the use of that distinct fraction of the hydrolysis gas which cannot be used for energy recovery (i.e. the $CO_2$-rich hydrolysis gas) within the process by utilizing it to purge percolators operated at offset times.

In addition to this, with the method according to the invention, the fraction of the hydrolysis gas containing methane can be used for energy recovery By monitoring the methane content present in the hydrolysis gas, and by using different modes of utilizing the hydrolysis gases depending on the gases contained therein (i.e. methane, $CO_2$) a considerable portion of the $CO_2$ unsuitable for energy recovery can be prevented from entering the biogas flow. In addition, by doing so, methane suitable for energy recovery is prevented from escaping idly into the atmosphere during biogas production. On the one band this ensures an improved economic use of the converted biogenic materials, and further prevents methane containing gas from escaping the gas-tight percolator in an uncontrolled manner when the percolator is opened, thus posing a safety risk, or adversely affecting the climate. On the other hand, by separating off a portion of the $CO_2$-rich fraction of the hydrolysis gas, the energy content of the raw biogas in the overall system is improved, which presents advantages for further gas utilisation.

Utilisation of the formed hydrolysis gas in the corresponding percolators designed to be gas-tight has the advantage of attaining an enhanced conversion of the biogenic materials used into biogas suitable for energy utilisation and of reducing their energetically unfavourable conversion to carbon dioxide and water in the percolator.

Thus, by using a method according to the invention, or a corresponding system according to the invention, compared to conventional biogas methods having one or two stages, a higher methane yield is obtained from the biogenic materials used, and a safe and environmentally friendly operation of the biogas plant is made possible.

If the method is carried out in a plant comprising several methane reactors, the method and performance of that plant can also be controlled more flexibly. Depending on demand, for example depending on the amount of biogenic material used, the performance can be regulated by switching methane reactors off or on. Within the plant, a smooth operation is possible, since the operation can continue even if one methane reactor is shut down (for example for maintenance).

BRIEF DESCRIPTION OF THE DRAWINGS

Based on the following figures and exemplary embodiments the invention is described in more detail, without restricting the invention to these.

DESCRIPTION OF PREFERRED EMBODIMENTS

EXAMPLE 1

Figure 1:
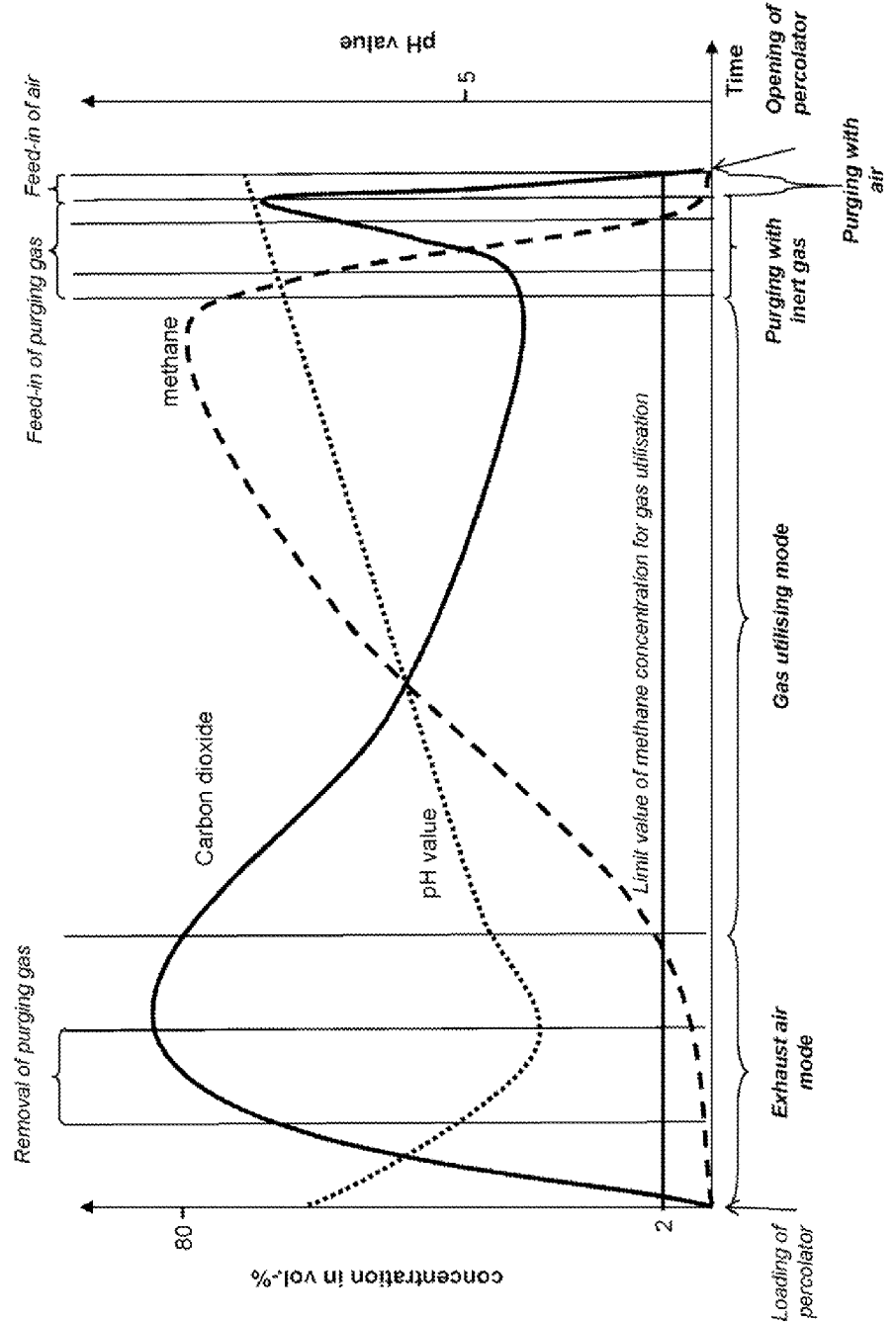
FIG. 1 Diagram of $CO_2$— and methane concentration, and of pH value development inside a percolator of a system according to the invention FIG. 2 Schematic of four gas-tight percolators connected in parallel in a system for obtaining biogas in two stages using a method according to the invention FIG. 3 Schematic of four gas-tight percolators connected serially in a system for obtaining biogas in two stages using a method according to the invention FIG. 4 Schematic of four gas-tight percolators connected in parallel in a system for obtaining biogas in two stages using a method according to the invention, with two methane reactors FIG. 5 Schematic of four gas-tight percolators connected serially in a system for obtaining. biogas in two stages using a method according to the invention, with two methane reactors
Figure 2:
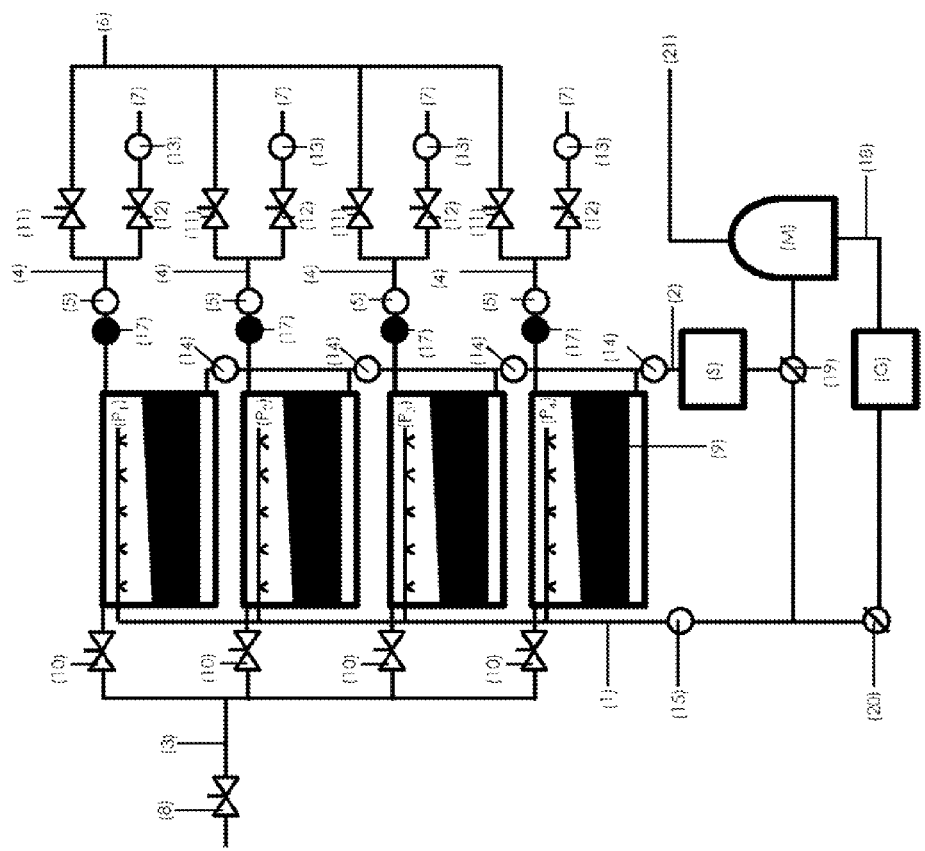

System According to the Invention for Obtaining Biogas in Two Stages, with Four Percolators Connected in Parallel The system according to the invention contains four hydrolysis reactors ($P_1$-$P_4$), being in this case solids percolators, as shown in FIG. 2, and one methane reactor. The percolators ($P_1$-$P_4$) are closed in a gas-tight manner, each percolator containing one gas supply pipe (3) and one as discharge pipe (4), which are placed in the upper part of each percolator, preferably on opposite sides.

The percolators ($P_1$-$P_4$) are each equipped with a grid or strainer bottom (9) on which the solid biogenic material which is to be percolated is deposited Furthermore each percolator ($P_1$-$P_4$) contains a liquids feed inlet (1) in its upper part, through which the liquid with which the solid biogenic material is sprinkled is fed in. Below the grid or strainer bottom (9) of each percolator ($P_1$-$P_4$) the corresponding hydrolysate discharge pipe (2) is arranged. Both the liquids feed inlet (1) and the hydrolysate discharge pipe (2) are each connected to one pH sensor (14, 15), which serves to determine the pH value of the liquid present in the pipe.

The hydrolysate discharge pipes (2) of the percolators ($P_1$-$P_4$) are connected. to each other, and are connected to the methane reactor (M) via a hydrolysate storage tank (5). Between the hydrolysate storage tank (S) and the methane reactor (M) a valve (19) is placed, which according to its adjustment allows liquids to flow into the methane reactor (M) or into the percolator (P) (via the liquids feed inlet (1)).

The methane reactor (M) comprises a biogas discharge pipe (21). A storage tank for fermentation liquid (G) is arranged downstream of the methane reactor (M) via the discharge pipe for fermentation liquid (18).

The liquids feed inlet (1) of the percolators ($P_1$-$P_4$) is connected to the storage tank for fermentation liquid (G) and the hydrolysate storage tank (S). In the liquids feed inlet (1) a pH-Sensor (15) is positioned to determine the pH value of the fed-in liquid. Furthermore, a valve (20) is arranged positioned in the liquids feed inlet (1).

The gas supply pipe (3) is equipped with a valve (8) and can deliberately he opened or closed, so that ambient air can enter the pipe. The gas supply pipes (3) of the individual percolators ($P_1$-$P_4$) are connected to each other, each of the gas supply pipes (3) having, near the opening into each percolator ($P_1$-$P_4$), a gas flap (10) can be opened separately, By opening the gas flaps (10) of two percolators a reciprocal exchange of gases between both percolators is possible.

Each gas discharge pipe (4) of the individual percolators ($P_1$-$P_4$) is connected to a measuring device (5), which serves to determine the quality and quantity of the gas inside the respective percolator ($P_1$-$P_4$), and measures the methane content of the gas present inside the percolator ($P_1$-$P_4$). Each gas discharge pipe (4) is branched and is each equipped with two valve elements (11, 12), which are connected to different functional units of the system.

The valves (11) are connected to a pipe leading to the system for energy recovery from the methane-containing hydrolysis gas (gas utilising system) (6), whereby optionally if necessary a storage tank for the methane-containing hydrolysis gas and/or a gas processing facility are interposed.

The valves (12) are each connected to an exhaust air system (7) via an exhaust fan (13). This allows for exhaust air to be extracted.

Each percolator ($P_1$-$P_4$) is equipped with a pressure sensor (17).

The system is operated as follows: The percolators ($P_1$-$P_4$) are loaded with solid biogenic material at offset times. The respective percolators ($P_1$-$P_4$) are closed. Via the liquids feed inlet (1) the solid biogenic material (i.e. substrate) in the percolator ($P_1$-$P_1$) is sprinkled with and passed by the percolation liquid (i.e. percolate and fermentation liquid) which is operated in circular flow operation. By feeding in the liquid, the degradable components of the substrate are being converted to alcohols, sugars and short-chain fatty acids, thereby being transformed into a water-soluble form. The degradable components of the substrate that are dissolved in the liquid hydrolysate are removed from the percolator via the hydrolysate discharge pipe (2). By means of the grid or strainer bottom (9) of the percolator ($P_1$-$P_4$) the sol id substrate is retained.

The circular flow operation is realized by feeding liquid from the hydrolysate storage tank (S) and/or the storage tank for fermentation liquid (G) via the liquids feed inlet (1) into the percolators ($P_1$-$P_4$).

Afterwards the hydrolysate is transferred to a hydrolysate storage tank (S). From there, it is either utilized again for percolation (by feeding it into the percolators ($P_1$-$P_4$) via the liquids feed inlet (1)) or it is, in a partial flow, continuously fed into the methane reactor (M), where fermentation to biogas containing methane and carbon dioxide takes place.

Towards the end of percolation, the amount of organic components of the biogenic material dissolved in the hydrolysate decreases, Therefore several percolators ($P_1$-$P_4$) are loaded at offset times, and the hydrolysates flowing out through each hydrolysate discharge pipe (2) are united in the hydrolysate storage tank (S). Doing so ensures that a continuous feed-in of organic decomposition products of the biogenic material into the methane reactor takes place.

By means of the gas-tight design of the percolators ($P_1$-$P_4$) the entry of atmospheric oxygen into the percolators ($P_1$-$P_4$) and the uncontrolled escape of hydrolysis gas are prevented.

The hydrolysis gas is removed via the gas discharge pipe (4). Via the measuring device (5) the contents of methane and carbon dioxide present in the hydrolysis gas are monitored.

Exhaust air mode: At the start of percolation the hydrolysis gas is $CO_2$-rich. At this point in time the pH value of the hydrolysate is strongly acidic The valve (12) is opened and the exhaust fan (13) is activated, The $CO_2$-rich hydrolysis gas is drawn off from the percolator Gas utilising mode: Over the further course of percolation, increasing amounts of methane are formed so that the methane content of the hydrolysis gas increases, while its $CO_2$ content decreases. if the methane content of the hydrolysis gas determined by the measuring device (5) exceeds a defined limit value, valve (12) is closed and valve (11) is opened. The methane-rich hydrolysis gas is fed into a gas utilising system (6), Preferably, it is collected beforehand in a storage tank and processed in a gas processing facility. At this point in time the pH value of the hydrolysate is in the neutral to slightly acidic range. The pH value is determined via each pH sensor (14) of the percolators ($P_1$-$P_4$).

Purging with inert gas (purging gas): Towards the end of percolation, only small amounts of organic degradation products of the biogenic material present in the hydrolysate are removed via the hydrolysate outlet (2). The pH value at the hydrolysate outlet (2) is approaching the pH value present at the liquids feed inlet (1). The pH value of the liquid is determined via pH sensors (14, 15). However, hydrolysis gas is still formed in smaller amounts, but comprising a significant methane content (methane-containing hydrolysis gas). For expelling (i.e. displacing) the remaining methane-containing hydrolysis gas from a percolator ($P_1$), $CO_2$-rich exhaust air ($CO_2$-rich hydrolysis gas) from another percolator operated at offset times and currently operated in exhaust air mode ($P_2$) is used.

To this end, first the gas flap (10) of the percolator ($P_1$) is closed either manually or by means of a process control system. The valve (12) connected to the gas utilising system (6) of the percolator ($P_1$) remains open.

The valve (11) of percolator ($P_2$) is closed (the valve (12) is also closed), so that the pressure within percolator ($P_2$) begins to increase due to the continuous production of gas. The pressure sensor (17) determines, preferably continuously, the pressure of the gas system within the percolator ($P_2$). If the pressure of the as system exceeds a previously defined threshold value, the gas flaps (10) of the percolators ($P_1$ and $P_2$) open. The percolators ($P_1$ and $P_2$) are thus connected at the front end.

Due to the overpressure inside the percolator ($P_2$) a directed exchange of gases from percolator ($P_2$) into percolator ($P_1$) takes place. Via the open valve (12) the gaseous mixture from percolator ($P_1$) is transported to the gas utilising system (6).

Once the methane concentration of the gaseous mixture formed by the hydrolysis gas and the inflowing $CO_2$-rich gas within the percolator ($P_1$) reaches a previously defined lower limit value, the valve (12) is closed. The methane concentration of the gaseous mixture in percolator ($P_1$) is thereby determined via the measuring device (5).

In case the methane concentration does not reach the lower limit value, the valve (12) can also be closed manually.

Purging with air. The air supply flaps (10) of the percolators ($P^4$, $P_4$) are closed, unless they are in the same phase of the process. The valve (11) of the percolator ($P_1$) and the valve (8) on the gas supply pipe (3) are opened, however, now ambient air is fed in via the gas supply pipe (3).

The exhaust fan (13) is switched on and serves to extract the gas present in the percolator ($P_1$). Via the measuring device (5) the gas composition in the percolator ($P_1$) is determined. As soon as the concentrations of methane and inert gas determined by the measuring device (5) have reached a previously defined respective minimal value (preferably less than 1 vol.-% for methane, preferably less than 1.5 vol.-% for $CO_2$), this signals that the percolator ($P_1$) can be opened, emptied and freshly loaded.

This fresh loading marks the start of a new cycle consisting of Exhaust air mode, Gas utilising mode, Purging and Opening.

EXAMPLE 2

Figure 3:
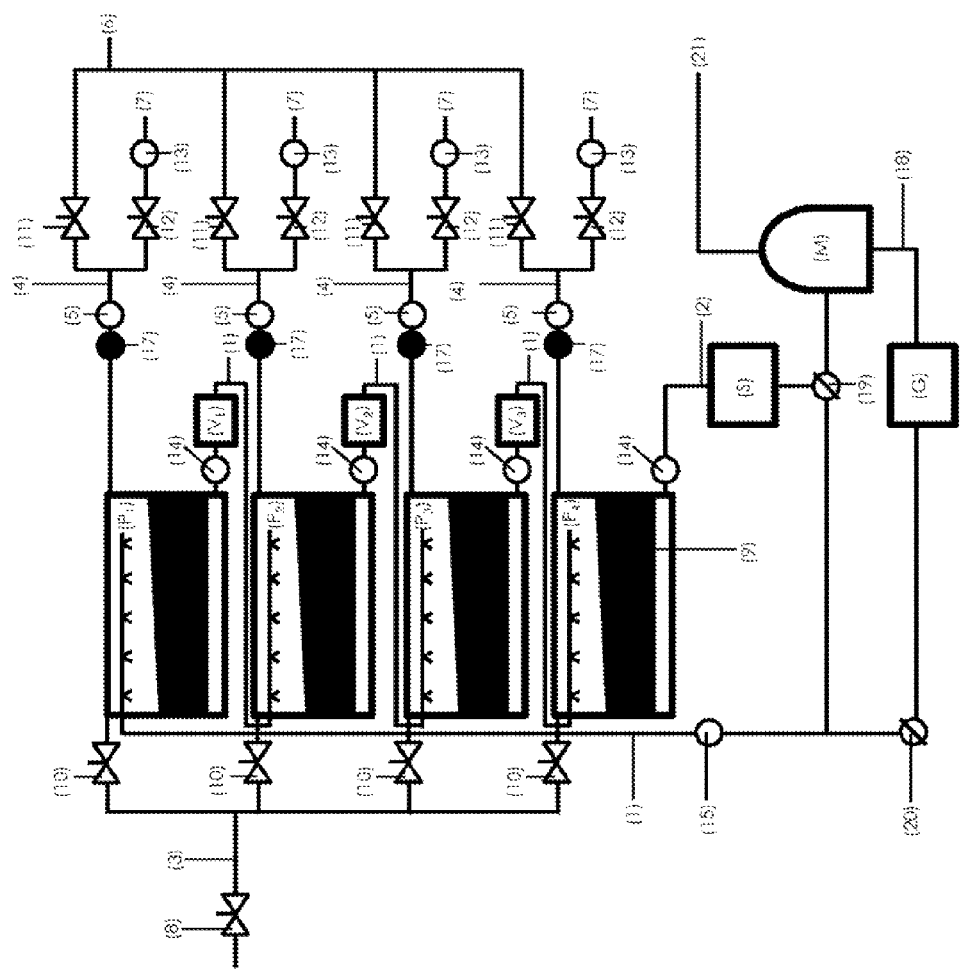

System According, to the Invention for Obtaining Biogas in Two Stages, having Four Serially Connected Percolators The system according to the invention contains four hydrolysis reactors ($P_1$-$P_4$), being in this case solids percolators, as shown in FIG. 3, and one methane reactor. The percolators ($P_1$-$P_4$) are closed in a gas-tight manner, each percolator containing one gas supply pipe (3) and one gas discharge pipe (4), which are placed in the upper part of each percolator, preferably on opposite sides.

The percolators ($P_1$-$P_4$) are each equipped with a grid or strainer bottom (9) on which the solid biogenic material which is to be percolated is deposited. Furthermore each percolator ($P_1$-$P_4$) contains a liquids feed inlet (1) in its upper part, through which the liquid with which the solid biogenic material is sprinkled is ted in. Below the arid or strainer bottom (9) of each percolator ($P_1$-$P_4$) the corresponding hydrolysate discharge pipe (2) is arranged. The hydrolysate discharge pipes (2) are each connected to a pH sensor (14) which serves to determine the pH value of the liquid present in the pipe.

The hydrolysate outlets (2) of the percolators ($P_1$-$P_3$) are each connected to a hydrolysate pre storage tank ($V_1$-$V_3$). The liquids feed inlet (1) of the percolator ($P_2$) is connected to the hydrolysate pre-storage tank ($V_1$). Correspondingly, the liquids feed inlet (1) of the percolator ($P_3$) is connected to the hydrolysate pre-storage tank ($V_2$), and the liquids feed inlet (1) of the percolator ($P_4$) is connected to the hydrolysate pre-storage tank ($V_3$).

The hydrolysate outlet (2) of the percolator ($P_4$) is connected to the methane reactor (M) via a hydrolysate storage tank (S). Between the hydrolysate storage, tank (S) and the methane reactor (M) a valve (19) is arranged, which according to its adjustment allows liquids to flow into the methane reactor (M) or into the percolator (P) (via the liquids feed inlet (1)).

The methane reactor (M) comprises a biogas discharge pipe (21) A storage tank for fermentation liquid (G) is arranged downstream of the methane reactor (M) via the discharge pipe for fermentation liquid (18).

The liquids feed inlet (1) of the percolator ($P_1$) is connected to the storage tank for fermentation liquid (G) and to the hydrolysate storage tank (S). In the liquids feed inlet (1) a pH-Sensor (15) is positioned to determine the pH value of the fed-in liquid Furthermore, a valve (20) is positioned in the liquids feed inlet (1).

The gas supply pipe (3) is equipped with a valve (8) and can deliberately be opened or dosed, so that ambient air can enter the pipe. The gas supply pipes (3) of the individual percolators ($P_1$-$P_4$) are connected to each other, each of the gas supply pipes (3) having, near the opening into each percolator ($P_1$-$P_4$), a gas flap (10), which can be opened separately. By opening the gas flaps (10) of two percolators a reciprocal exchange of gases between both percolators is possible.

Each gas discharge pipe (4) of the individual percolators ($P_1$-$P_4$) is connected to a measuring device (5), which serves to determine the quality and quantity of the gas inside the respective percolator ($P_1$-$P_4$), and measures the methane content of the gas present inside the percolator ($P_1$-$P_4$). The gas discharge pipe (4) is branched and is equipped with two valve elements (11, 12), which are connected to different functional units of the system.

The valves (11) are connected to a pipe leading to the system for energy recovery from the methane-containing hydrolysis gas (gas utilising system) (6), whereby optionally a storage tank for the methane-containing hydrolysis gas and/or a gas processing facility are interposed.

The valves (12) are each connected to an exhaust air system (7) via an exhaust fan (13) This allows for exhaust air to be extracted.

Each percolator ($P_1$-$P_4$) is equipped with a pressure sensor (17).

The system is operated as follows: The percolators ($P_1$-$P_4$) are loaded with solid biogenic material at offset times. In this process, percolator ($P_4$) is loaded first, followed by the percolators ($P_3$-$P_1$) in this order. Each of the percolators ($P_1$-$P_4$) is closed after having been loaded.

Via the liquids feed inlet (1) the solid biogenic material (i.e. substrate) in the percolator ($P_1$-$P_4$) is sprinkled with and passed by the percolation liquid (i.e. percolate and fermentation liquid) which is operated in circular flow operation. By feeding in the liquid, the degradable components of the substrate are being converted to alcohols, sugars and short-chain fatty acids, thereby being transformed into a water-soluble form. The degradable components of the substrate that are dissolved in the liquid hydrolysate are removed from the percolator via the hydrolysate discharge pipe (2). By means of the grid or strainer bottom (9) of the percolator ($P_1$-$P_4$) the solid substrate is retained.

The circular how operation is realized by feeding in liquid from the hydrolysate storage tank (S) and/or the storage tank for fermentation liquid (6) via the liquids feed inlet (1) into the percolator ($P_1$). Due to the serial connection of the percolators, in each case the hydrolysate removed from one percolator is fed into another percolator, which has been loaded with biogenic material at an earlier point in time. To this end, hydrolysate from percolator ($P_1$) is transported into percolator ($P_2$) via the hydrolysate pre-storage tank ($V_1$). A corresponding process takes place for feeding in liquids into the percolators ($P_3$) and ($P_4$).

The hydrolysate from percolator ($P_4$) is transported into a hydrolysate storage tank (S). From there, it is either utilized again for percolation (by feeding it into the percolator ($P_1$) via the liquids feed inlet (1) of ($P_1$)) or it is, in the partial flow, continuously fed into the methane reactor (M), where fermentation to biogas containing methane and carbon dioxide takes place.

Towards the end of percolation, the amount of organic components of the biogenic material dissolved in the hydrolysate decreases. Therefore several percolators ($P_1$-$P_4$) are loaded at offset times. Doing so ensures that a continuous feed-in of organic decomposition products of the biogenic material into the methane reactor takes place.

By means of the gas-tight design of the percolators ($P_1$-$P_4$) the entry of atmospheric oxygen into the percolators ($P_1$-$P_4$) and the uncontrolled escape of hydrolysis gas are prevented.

The hydrolysis gas is removed from the percolators ($P_1$-$P_4$) via the gas discharge pipe (4). Via the measuring device (5) the contents of methane and carbon dioxide present in the hydrolysis gas are monitored.

Exhaust air mode: At the start of percolation the hydrolysis gas is $CO_2$-rich. At this point in time the pH value of the hydrolysate is strongly acidic. The valve (12) is opened and the exhaust fan (13) is activated. The $CO_2$-rich hydrolysis gas is drawn off from the percolator ($P_1$-$P_4$).

Gas utilising mode: Over the further course of percolation, increasing amounts of methane are formed so that the methane content of the hydrolysis gas increases, while its $CO_2$ content decreases, if the methane content of the hydrolysis gas determined by the measuring device (5) exceeds a defined limit value, valve (12) is closed and valve (11) is opened The methane rich hydrolysis gas is fed into a as utilising system (6), Preferably, it is collected beforehand in a storage tank and processed in a gas processing facility. At this point in time the pH value of the hydrolysate is in the neutral to slightly acidic range. The pH value is determined via each pH sensor (14) of the percolators ($P_1$-$P_4$).

Purging with inert gas (purging gas): Towards the end of percolation, only small amounts of organic degradation products of the biogenic mated al present in the hydrolysate are removed via the hydrolysate outlet (2). The pH value at the hydrolysate outlet (2) is approaching the pH value present at the liquids feed inlet (1). The pH value of the liquid is determined via pH sensors (14, 15). However, hydrolysis gas is still formed in smaller amounts, but comprising a significant methane content (methane-containing hydrolysis For expelling (i.e. displacing) the remaining methane-containing hydrolysis gas from a percolator ($P_2$), the $CO_2$-rich exhaust air ($CO_2$-rich hydrolysis gas) from another percolator operated at offset times and currently operating in exhaust an mode ($P_1$) is used To this end, first the gas flap (10) of the percolator ($P_2$) is closed either manually or by means of a process control system. The valve (12) connected to the gas utilising system (6) of the percolator ($P_2$) remains open.

The valve (11) of percolator ($P_1$) is closed (the valve (12) is also closed), so that the pressure within percolator ($P_1$) begins to increase due to the continuous production of gas. The pressure sensor (17) determines, preferably continuously, the pressure of the gas system within the percolator ($P_1$). If the pressure of the gas system exceeds a previously defined threshold value, the gas flaps (10) of the percolators ($P_2$ and $P_1$) open. The percolators ($P_2$ and $P_1$) are thus connected at the front end.

Due to the overpressure inside the percolator ($P_1$) a directed exchange of gases from percolator ($P_1$) into percolator ($P_2$) takes place. Via the open valve (12) the gaseous mixture from percolator ($P_2$) is transported to the as utilising, system (6).

Once the methane concentration of the gaseous mixture formed by the hydrolysis gas and the inflowing $CO_2$-rich as within the percolator (P) reaches a previously defined lower limit value, the valve (12) is closed. The methane concentration of the gaseous mixture in percolator ($P_2$) is thereby determined via the measuring device (5)

In case the methane concentration does not reach the lower limit value, the valve (12) can also be closed manually.

Purging with air: The air supply flaps (10) of the percolators ($P_3$, $P_4$) are closed, unless they are in the same phase of the process. The valve (11) of the percolator ($P_2$) and the valve (8) on the gas supply pipe (3) are opened; however, now ambient air is fed in via the gas supply pipe (3).

The exhaust fan (13) is switched on and serves to extract the gas present in the percolator ($P_2$). Via the measuring de ice (5) the gas composition in the percolator $P_2$) is determined. As soon as the concentrations of methane and inert gas determined by the measuring device (5) have reached a previously defined respective minimal value (preferably less than 1 vol-% for methane, preferably less than 1.5 vol.-% for $CO_2$), this signals that the percolator ($P_2$) may be opened, emptied and freshly loaded.

This fresh loading marks the start of a new cycle consisting of Exhaust air mode, Gas utilising mode, Purging and Opening.

EXAMPLE 3

Figure 4:
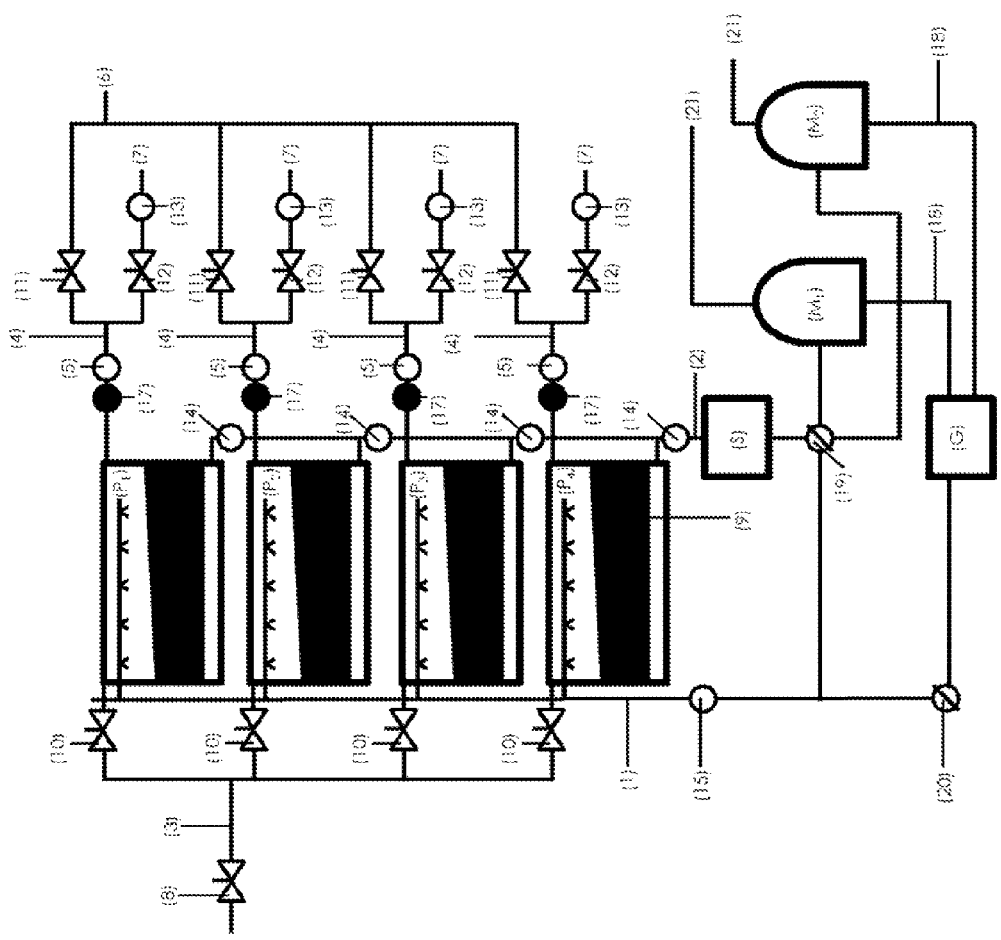

System According to the Invention for Obtaining Biogas in Two Stages, with Four Percolators Connected in Parallel, with Two Methane Reactors The system contains four hydrolysis reactors ($P_1$-$P_4$), being in this case solids percolators, as shown in FIG. 4, and two methane reactors. The system is designed in analogy to Example 1, and is operated in the same manner. However, the difference between this system and that of Example 1 consists in the arrangement of two methane reactors ($M_1$, $M_2$). These are arranged downstream of the hydrolysate storage tank (S) and connected to it via each methane reactor's ($M_1$, $M_2$) hydrolysate feed inlet. Via the valve (19) switching the hydrolysate feed into methane reactor ($M_1$) or methane reactor ($M_2$) is possible. Each of the methane reactors ($M_1$, $M_2$) comprises a biogas discharge pipe (21). The storage tank for fermentation liquid (G) is arranged downstream of the methane reactors ($M_1$, $M_2$) via their discharge pipes for fermentation liquid (18).

During operation, the hydrolysate from the hydrolysate storage tank (S) is fed into one of the methane reactors. The fermentation liquid is transported from the methane reactors ($M_1$, $M_2$) into the storage tank for fermentation liquid (G).

EXAMPLE 4

Figure 5:
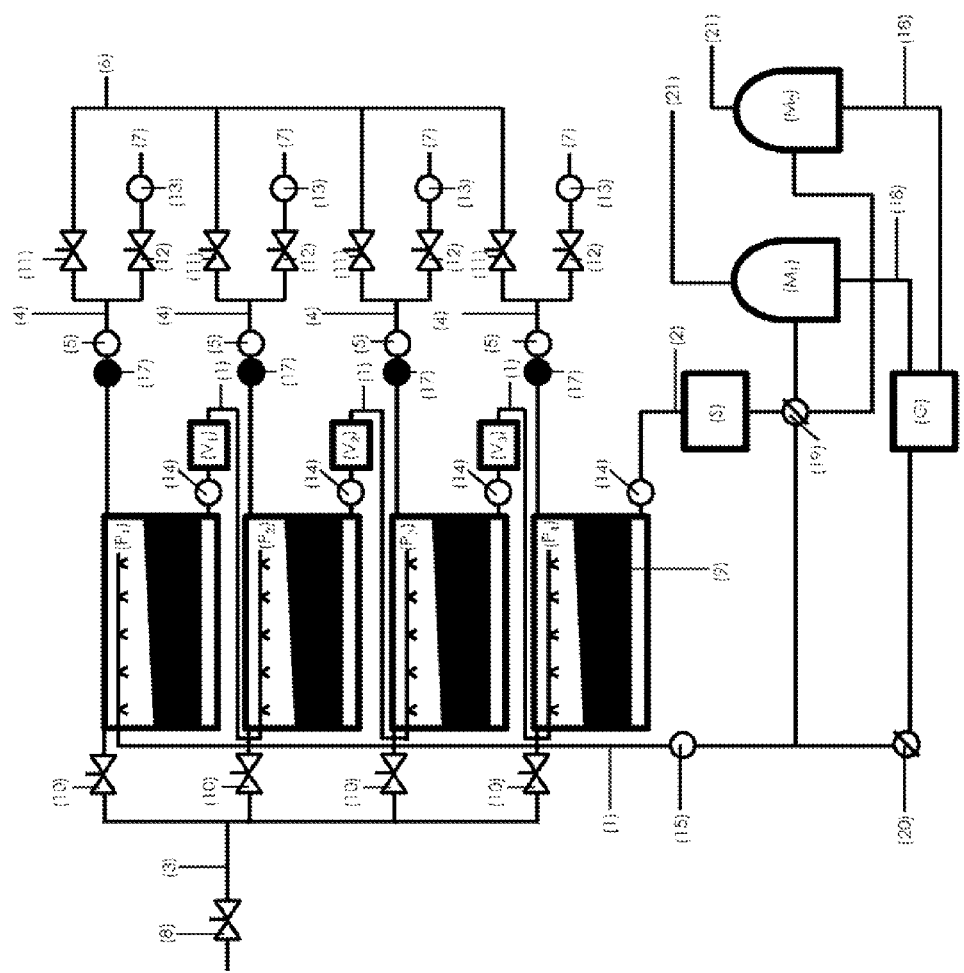

System According to the Invention for Obtaining Biogas in Two Stages, with Four Percolators Connected Serially, with Two Methane Reactors The system contains four hydrolysis reactors ($P_1$-$P_4$), being in this case solids percolators, as shown in FIG. 5, and two methane reactors. The system is designed in analogy to Example 2, and is operated in the same manner. However, the difference between this system and that of Example 2 consists in the arrangement of two methane reactors ($M_1$, $M_2$). These are arranged downstream of the hydrolysate storage tank (S) and connected to it via each methane reactor's ($M_1$, $M_2$) hydrolysate feed inlet Via the valve (19) switching the hydrolysate feed into methane reactor ($M_1$) or methane reactor ($M_2$) is possible. Each of the methane reactors ($M_1$, $M_2$) comprises a biogas discharge pipe (21). The storage tank for fermentation liquid (G) is arranged downstream of the methane reactors ($M_1$, $M_2$) via their discharge pipes for fermentation liquid (18).

During operation, the hydrolysate from the hydrolysate storage tank (S) is fed into one of the methane reactors. The fermentation liquid is transported from the methane reactors ($M_1$, $M_2$) into the storage tank for fermentation liquid (G).

List of Reference Numbers
- (1) liquids feed inlet.
- (2) hydrolysate outlet (hydrolysate discharge pipe)
- (3) gas supply pipe
- (4) gas discharge pipe
- (5) measuring device determining quality and amount of gas
- (6) gas utilising system
- (7) exhaust air system
- (8) valve
- (9) grid or strainer bottom
- (10) gas flap
- (11) valve
- (12) valve
- (13) exhaust fan
- (14) pH sensor
- (15) pH sensor
- (16) valve
- (17) pressure sensor
- (18) discharge pipe for fermentation liquid
- (19) valve
- (20) valve
- (21) biogas discharge pipe
- (G) storage tank for fermentation liquid
- (M) methane reactor
- ($M_x$) methane reactor of a system comprising x methane reactors, with x≥1
- (P) percolator
- ($P_n$) percolator of a system comprising n percolators, with n≥1
- (S) hydrolysate storage tank
- (V) hydrolysate pre-storage tank
- ($V_n$) hydrolysate pre-storage tank of a system comprising n hydrolysate pre-storage tanks, with n≥1

What is claimed is:

1. A method for obtaining biogas in two or more stages by hydrolysis of solid biogenic material in at least two percolators operated at offset times, comprising a hydrolysis stage and a methane stage, the method comprising:
hydrolyzing biogenic material in the hydrolysis stage to form in the percolator liquid hydrolysate and hydrolysis gas, at first $CO_2$-rich hydrolysis gas being formed and afterwards methane-containing hydrolysis gas being formed,
removing the hydrolysate from the percolators and collecting the hydrolysate,
feeding one part of the hydrolysate into the methane stage and feeding the other part of the hydrolysate into the hydrolysis stage,
converting the hydrolysate in the methane stage into biogas and fermentation liquid by methane-forming microorganisms,
removing the fermentation liquid from the methane reactor and collecting the fermentation liquid and optionally feeding the fermentation liquid into the hydrolysis stage,
operating the percolators gas-tightly, and
drawing hydrolysis gas off from the percolators,
using methane-containing hydrolysis gas for energy recovery, and
using $CO_2$-rich hydrolysis gas with a $CO_2$ content of at least 50 vol.-% and a methane content of less than 2 vol.-% from one percolator for the first five to nine days of percolation for purging another percolator, which is operated at offset times.

2. The method according to claim 1, wherein operating the percolators comprises in the following order:
a. Loading the percolator with the biogenic material,
b. Employing an exhaust air mode,
c. Employing a gas utilising mode,
d. Purging the percolator with exhaust air from another percolator that is operated at offset times,
e. Purging the percolator with air,
f. Opening the percolator,
wherein in the exhaust air mode the hydrolysis gas is drawn off as exhaust air from the percolator, whereby in the gas utilising mode the hydrolysis gas is drawn off from the percolator and is used for energy recovery, and wherein the hydrolysis gas present inside the percolator during purging in step d. is removed by expelling the hydrolysis gas by feeding in exhaust air from a percolator that is operated at offset times.

3. The method according to claim 2, further comprising the step of continuing the exhaust air mode until the methane concentration of the gas present inside the percolator reaches a previously defined limit value and/or until the pH value of the hydrolysate reaches a previously defined limit value.

4. The method according to claim 3, further comprising the step of continuing the gas utilising mode until the methane concentration of the gas present inside the percolator is lower than the limit value.

5. The method according to claim 2, wherein the at least two percolators operated at offset times are operated such that at least one percolator is operated in the exhaust air mode.

6. The method according to claim 5, wherein, before purging one percolator, another percolator that is operated at offset times in relation to the percolator to be purged and is operated in the exhaust air mode, is closed, so that overpressure arises in this percolator, and after reaching a threshold value of the pressure, the exhaust air is subsequently transported due to the overpressure from the percolator operated at offset times into the percolator to be purged.

7. A system for obtaining biogas in two or more stages, comprising:
at least two percolators ($P_1$, $P_2$), each comprising one hydrolysate discharge pipe (2) and one liquids feed inlet (1), the hydrolysate discharge pipe (2) connected to at least one methane reactor (M) via at least one storage tank for hydrolysate (S),
at least one storage tank for fermentation liquid (G) connected via a discharge pipe for fermentation liquid (18) downstream of the at least one methane reactor,
the storage tank for hydrolysate (S) and the storage tank for fermentation liquid (G) connected to the respective liquids feed inlet (1) of the percolator ($P_1$, $P_2$),
the at least two percolators ($P_1$, $P_2$) being gas-tight and each comprising at least one closable gas supply pipe (3) and at least one closable gas discharge pipe (4), the percolators ($P_1$, $P_2$) each connected to a methane sensor which serves to measure the methane content of the gas present in the respective percolator ($P_1$, $P_2$) and each connected to a pH sensor (14), which serves to measure the pH value of the liquid present in the respective percolator ($P_1$, $P_2$), wherein the gas supply pipe (3) of the respective percolator ($P_1$, $P_2$) is designed to switch to air supply, to gas supply from another percolator, or to close the gas supply pipe, the at least two percolators ($P_1$, $P_2$) connected to each other via their gas supply pipes (3) so that during operation at offset times the feed-in of $CO_2$-rich hydrolysis gas from one percolator ($P_1$) in exhaust air mode into a percolator to be purged ($P_2$) is enabled.

8. The system according to claim 7, wherein the percolators ($P_1$, $P_2$) each comprise a closable gas discharge pipe (4), the gas discharge pipe (4) designed to allow switching to gas discharge into a system for energy utilisation, or discharge of the off-gas into the atmosphere, or closure of the gas discharge pipe.

9. The system according to claim 7, wherein a pressure sensor (17) is arranged at each of the percolators ($P_1$, $P_2$) to measure the pressure inside the percolator ($P_1$, $P_2$).

\* \* \* \* \*